(12) United States Patent
Hoke et al.

(10) Patent No.: US 9,833,380 B2
(45) Date of Patent: Dec. 5, 2017

(54) NASAL IRRIGATION DEVICE AND SYSTEM WITH FAUX COLLAPSIBLE CARTRIDGE ELEMENT

(75) Inventors: Martin R. Hoke, Lakewood, OH (US); Robert D. Schilling, Olmsted Township, OH (US); Patrick W. Brown, Auburn, OH (US); Jeffrey S. Taggart, Cleveland Heights, OH (US)

(73) Assignee: RhinoSystems, Inc., Cleveland, OH (US)

( * ) Notice: Subject to any disclaimer, the term of this patent is extended or adjusted under 35 U.S.C. 154(b) by 1263 days.

(21) Appl. No.: 13/551,274

(22) Filed: Jul. 17, 2012

(65) Prior Publication Data

US 2012/0330239 A1 Dec. 27, 2012
US 2017/0239429 A9 Aug. 24, 2017

Related U.S. Application Data

(63) Continuation-in-part of application No. 13/276,448, filed on Oct. 19, 2011, which is a continuation of (Continued)

(51) Int. Cl.
*A61M 3/02* (2006.01)
*A61H 35/04* (2006.01)
(Continued)

(52) U.S. Cl.
CPC .......... *A61H 35/04* (2013.01); *B65D 75/326* (2013.01); *A61H 2033/048* (2013.01);
(Continued)

(58) Field of Classification Search
CPC ........ A61H 2033/048; A61H 2201/105; A61H 2202/182; A61H 2205/023; A61H 35/04;
(Continued)

(56) References Cited

U.S. PATENT DOCUMENTS 1,248,891 A 12/1917 Nichols
1,487,252 A 3/1924 Lore
(Continued)

FOREIGN PATENT DOCUMENTS

WO WO2008/058160 A2 5/2008

OTHER PUBLICATIONS

International Search Report for International Application No. PCT/US2012/047055, dated Dec. 7, 2012.
(Continued)

*Primary Examiner* — Anthony Stashick
*Assistant Examiner* — Mollie Impink
(74) *Attorney, Agent, or Firm* — Fay Sharpe LLP

(57) ABSTRACT

A nasal irrigation device communicates an irrigant to a device user and comprises a mechanics module and a reservoir assembly wherein a source of saline comprising a cartridge is disposed within the mechanics module adjacent a lid assembly for piercing the cartridge upon closing of a lid for releasing the cartridge contents into the reservoir assembly. A faux collapsible cartridge for testing operability of a nasal irrigation device comprises a housing including a shaft, a spring biased rod extending from the housing shaft, and a flange depending from a housing wall whereby the rod and flange are disposed to actuate a trigger assembly of the nasal irrigation device.

6 Claims, 9 Drawing Sheets

Related U.S. Application Data application No. 12/042,906, filed on Mar. 5, 2008, now Pat. No. 8,048,023.

(60) Provisional application No. 61/508,767, filed on Jul. 18, 2011, provisional application No. 60/895,180, filed on Mar. 16, 2007, provisional application No. 60/893,191, filed on Mar. 6, 2007.

(51) Int. Cl.
*B65D 75/32* (2006.01)
*A61M 15/00* (2006.01)
*A61H 33/04* (2006.01)

(52) U.S. Cl.
CPC .. *A61H 2201/105* (2013.01); *A61H 2205/023* (2013.01); *A61M 15/009* (2013.01)

(58) Field of Classification Search
CPC ........... A61M 15/009; A61M 2202/04; A61M 35/003; B65D 51/002; B65D 75/326; B65D 75/365; B65D 75/366; B65D 77/30; B65D 77/38; B65D 77/40; B65D 85/8043
USPC ....................................................... D9/425
See application file for complete search history.

(56) References Cited

U.S. PATENT DOCUMENTS

| | | | |
|---|---|---|---|
| 1,502,163 A | 7/1924 | Sprague | |
| 1,603,758 A | 10/1926 | Fisher | |
| 1,607,726 A | 11/1926 | De Suszko | |
| 2,078,180 A | 4/1937 | Kronenberg | |
| 2,280,992 A | 4/1942 | Wright et al. | |
| 4,029,095 A | 6/1977 | Pena | |
| D270,283 S | 8/1983 | Goodnow et al. | |
| 4,403,611 A | 9/1983 | Babbitt et al. | |
| 4,637,814 A | 1/1987 | Leiboff | |
| 4,655,197 A | 4/1987 | Atkinson | |
| 5,746,721 A | 5/1998 | Pasch et al. | |
| 5,788,683 A | 8/1998 | Martin | |
| 5,899,878 A | 5/1999 | Glassman | |
| 5,928,190 A | 7/1999 | Davis | |
| 6,099,494 A | 8/2000 | Henniges et al. | |
| D440,874 S * | 4/2001 | Shurtleff | D9/425 |
| 6,419,662 B1 | 7/2002 | Solazzo | |
| 6,520,384 B2 | 2/2003 | Mehta | |
| 6,540,718 B1 | 4/2003 | Wennek | |
| 6,561,188 B1 | 5/2003 | Ellis | |
| 6,669,059 B2 | 12/2003 | Mehta | |
| 6,688,497 B2 | 2/2004 | Mehta | |
| 6,715,485 B1 | 4/2004 | Djupesland | |
| 6,736,792 B1 | 5/2004 | Liu | |
| 6,748,944 B1 | 6/2004 | Dellavecchia et al. | |
| 6,907,879 B2 | 6/2005 | Drinan et al. | |
| 7,029,705 B2 | 4/2006 | Fuhr | |
| 7,981,077 B2 | 7/2011 | Hoke et al. | |
| D702,548 S * | 4/2014 | Flury | D9/425 |
| 2002/0151836 A1 | 10/2002 | Burden | |
| 2005/0028812 A1 | 2/2005 | Djupesland | |
| 2008/0119782 A1 | 5/2008 | Steinman et al. | |
| 2008/0154183 A1 | 6/2008 | Baker et al. | |
| 2008/0183128 A1 | 7/2008 | Morriss et al. | |
| 2008/0208112 A1 | 8/2008 | Benoussan | |
| 2008/0221507 A1 | 9/2008 | Hoke et al. | |
| 2008/0283439 A1 * | 11/2008 | Sullivan | A61M 15/0028 206/531 |
| 2009/0281485 A1 | 11/2009 | Baker et al. | |

OTHER PUBLICATIONS

Supplementary Partial European Search Report dated Jun. 10, 2015.

* cited by examiner

NASAL IRRIGATION DEVICE AND SYSTEM WITH FAUX COLLAPSIBLE CARTRIDGE ELEMENT

This application claims the priority benefit of U.S. application Ser. No. 61/508,767, filed Jul. 18, 2011. This application is a continuation-in-part of U.S. application Ser. No. 13/276,448, filed Oct. 19, 2011, which is a continuation of U.S. application Ser. No. 12/042,906, filed Mar. 5, 2008, now U.S. Pat. No. 8,048,023, which claims priority from U.S. application Ser. No. 60/893,191, filed Mar. 6, 2007 and 60/895,180 filed Mar. 16, 2007.

TECHNICAL FIELD

The presently disclosed embodiments generally relate to methods and devices for lavaging, irrigating, rinsing, and hydrating the nasal cavity and anatomical openings thereto, generally and popularly known as nasal lavage or nasal irrigation.

BACKGROUND

Nasal and sinus disease and sinus related syndromes and symptoms are a common clinical problem with considerable patient morbidity, substantial direct costs, and a significant, negative impact on the quality of life for those who are afflicted. The four primary categories of afflicted groups are: 1) individuals with acute and chronic rhinosinusitis; 2) individuals with upper respiratory infections, 3) individuals who suffer from allergic rhinitis; and 4) individuals with chronic snoring problems. These four categories amount to millions of people who suffer from nasal congestion on a daily basis.

Bathing the nasal and sinus cavities with lightly-salted water to wash away encrusted mucous, irritants, and foreign particles, and to shrink the turbinates for the purpose of improving airflow and relieving nasal congestion has been widely practiced across many cultures for literally thousands of years. More recently, and particularly since about 1990, a significant number of peer-reviewed clinical trials have been undertaken at leading American and European medical schools and research centers testing whether the anecdotal claims of relief from the symptoms of nasal maladies as a result of practicing nasal irrigation, are well founded and pass scientific scrutiny.

These studies indicate that nasal irrigation is a clinically proven method for treating the symptoms of sinus-related disease by exposing the nasal cavity to a streaming volume of saline. While the exact mechanism by which nasal irrigation's effectiveness is achieved is not yet well understood by the medical and scientific research community, it is likely multifaceted and includes a number of physiological effects which individually or in concert may result in an improved ability of the nasal mucosa to reduce the pathologic effects of inflammatory mediators and other triggers of allergic rhinitis, asthma and other chronic mucosal reactions, as follows. First, it rinses the entire interior of the nasal cavity, washing away encrustations that may be blocking the multiple ostia that connect the sinus cavities to the nasal cavity, thereby allowing the sinus cavities to properly drain into the nasal cavity and making the sinus cavities a much less attractive breeding ground for the colonization of bacteria. Second, it decreases the viscosity of the mucous in the nasal cavity, thereby greatly reducing the formation of interior encrustations. Third, it leaves a small residue of saline on the interior surfaces of the nasal cavity, including the openings to the sinus cavities and sometimes in the sinus cavities themselves. This is beneficial because saline has an inherently antiseptic quality that hinders the growth of bacteria. Fourth, exposure of the turbinates, vascular tissue that warms and humidifies the air inspired through the nose before it reaches the lungs, to saline causes them to reduce in size, thereby reducing nasal congestion. Fifth, it improves mucociliary clearance as a result of increased ciliary beat frequency, which improves the ability of the mucosa to perform its natural, flushing function. Sixth, the saline may wash away airborne bacteria, viral particles, irritants and other foreign particles that cause infections and allergies.

There are two methods by which the nasal cavity can be irrigated: pressure that is positive relative to atmospheric pressure, and pressure that is negative relative to atmospheric pressure. Positive pressure can be effected two ways: first, by gravity, and second, by means of manufactured pressure. Negative pressure, also called vacuum or suction, can also be effected two ways: first, anatomically by nasal inhaling or sniffing, and second, by means of manufactured suction.

Positive pressure devices that rely on gravity allow the flow of saline into the nasal cavity by, for example, inserting the tip of a teapot-like spout into one nostril and pouring the saline into it. The saline then flows around the posterior margin of the nasal septum and out the other nostril of the user. An example of a gravity-based device is the neti pot. However, the awkward physical position required to accomplish such a rinse is difficult for many people, and the free flowing effluent from the nasal passageway is messy so that substantial clean up procedures are necessary.

Positive pressure devices that rely on manufactured pressure pump the saline into the nasal cavity, again, by introducing the saline into one nostril, forcing it under manufactured pressure around the posterior margin of the nasal septum, and allowing it to drain out the other nostril. This can be achieved, for example, by placing the nozzle of a saline-filled, flexible plastic bottle into one nostril and squeezing it, thereby injecting the saline into one nostril, through the nasal cavity, and out the other nostril. This can also be achieved by similarly forcing saline into the nasal cavity under pressure created by a mechanical pump. Although this method avoids some of the physical awkwardness needed to achieve a gravity forced flow, the problems of messiness and the attendant inconvenience of cleaning remain. In addition, the varied pressures imparted by a squeeze bottle can impart undesired, painful, and even harmful pressures throughout the nasal passageway, and particularly on the Eustachian tube ostia. Thus, this requires some acquired skill for proper use.

Earlier nasal lavage devices that relied on negative, manufactured pressure drew a saline solution through the nasal cavity by imparting suction to a receptacle bottle or directly to the nasal cavity, but such devices are large, non-portable, complex, difficult to operate, and generally require the supervision and assistance for operation of an attending physician or medical assistant.

There is presently no practical device that offers a user the ability to practice nasal lavage using either or both positive and negative pressure, whether gravitational, anatomical, or manufactured, or any combination thereof, in a single hand-held collection device.

There is a need for a nasal irrigation device for communicating an irrigant to a device user comprising a mechanics module and a reservoir assembly wherein a source of saline comprising a cartridge is disposed within the mechanics module adjacent a lid assembly for piercing the cartridge upon closing of the lid for releasing the cartridge contents into the reservoir assembly.

There is a need for a convenient handheld device that can safely irrigate the nasal cavity with a controlled, gentle supply, draw the irrigant through the nasal cavity under the influence of gentle powered suction, collect the effluent safely in a manner facilitating quick and easy disposal, and is readily adaptable to a wide variety of nasal dimensions.

There is a need for a device that uses a readily transportable capsule for effecting the filling of the device with irrigant.

DETAILED DESCRIPTION

Figure 1:
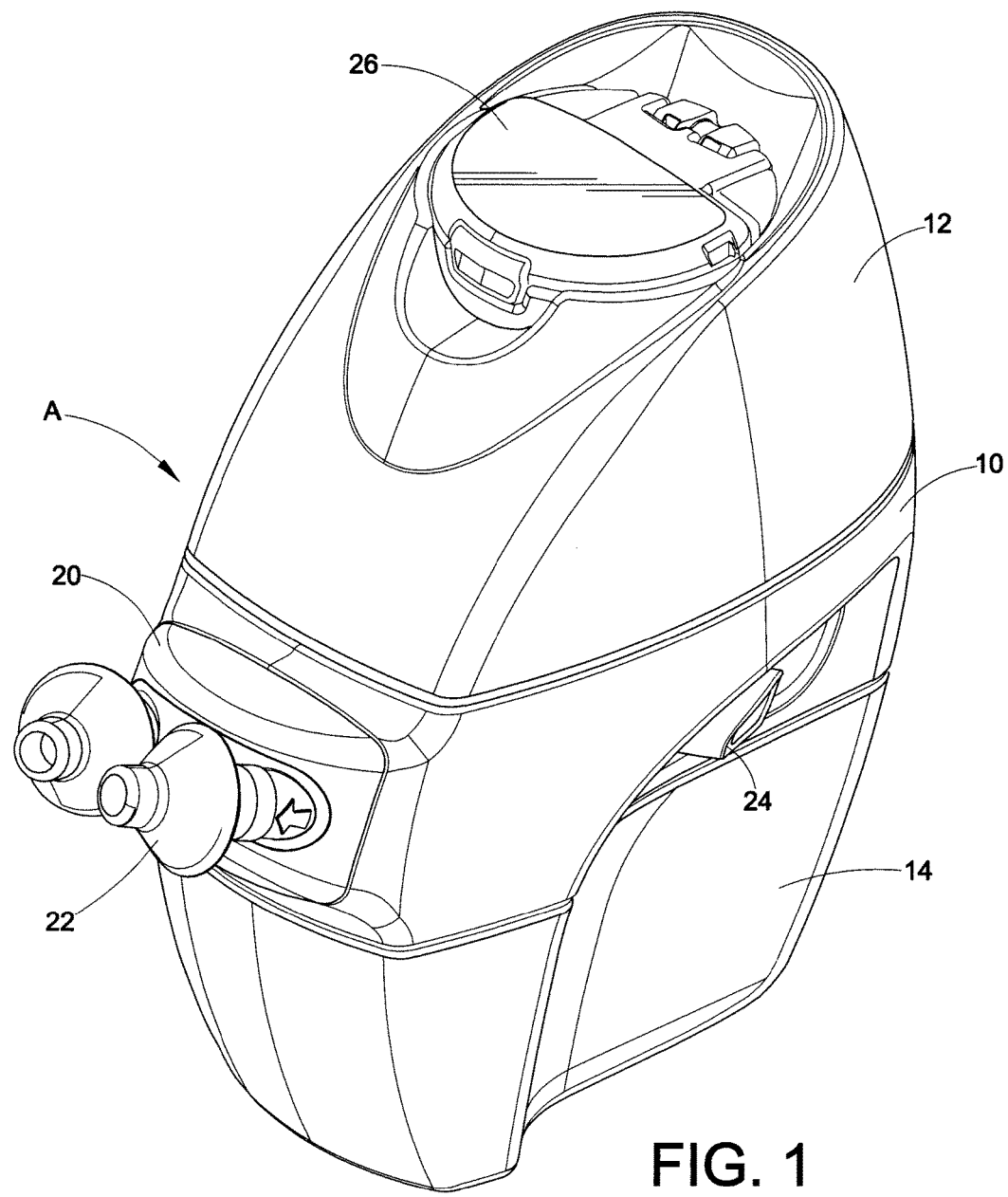
FIG. 1 is a perspective view of an embodiment of a nasal irrigation device and system.

FIG. 1 shows a nasal irrigation device or controller A wherein a preferably saline solution is communicated to the nasal cavity of a user for irrigating and washing the cavity, and upon departure from the cavity is collected in a collection reservoir. Such a saline based therapy is well known in itself, but the subject delivery system is novel in that it uses a disposable cartridge concentrate supply for enhanced portability of the tool as opposed to a device that would require a bottle of saline solution. Such known systems have used ready-made supply bottles, or mixing of salt packs in squeeze bottles or neti pots. The irrigation device A is comprised of three principal components, a mechanics module assembly 10, an upper reservoir assembly 12 and a lower reservoir assembly 14. The mechanics module 10 includes a nasal interface 20 for engaging the nostrils of a user with nasal pillows or nozzles 22 that are partially inserted into the nostrils and sealed against the opening perimeters thereof, as will be more fully explained below. An on/off switch 24 actuates a miniature pump for evacuating the lower reservoir 14 and applying differential pressure to the lower reservoir 14 and the nasal cavity of a user, and a fluid release valve 72 (FIG. 4) to facilitate the flow of the saline through the whole fluid passageway from the upper reservoir to the lower reservoir. Switch 24 is preferably a two stage actuator wherein a first stage starts the pump and the second stage opens the valve 72 to the flow of fluid from the upper reservoir, through the mechanics module and ultimately to the lower reservoir. Saline mix to form an isotonic saline solution for the irrigating results from water being poured into the upper reservoir 12 through opening of the hinged lid 26, and the insertion of a saline concentrate capsule (FIG. 5) so that upon closing of the lid, the concentrate falls into mixture with the water.

Figure 2:
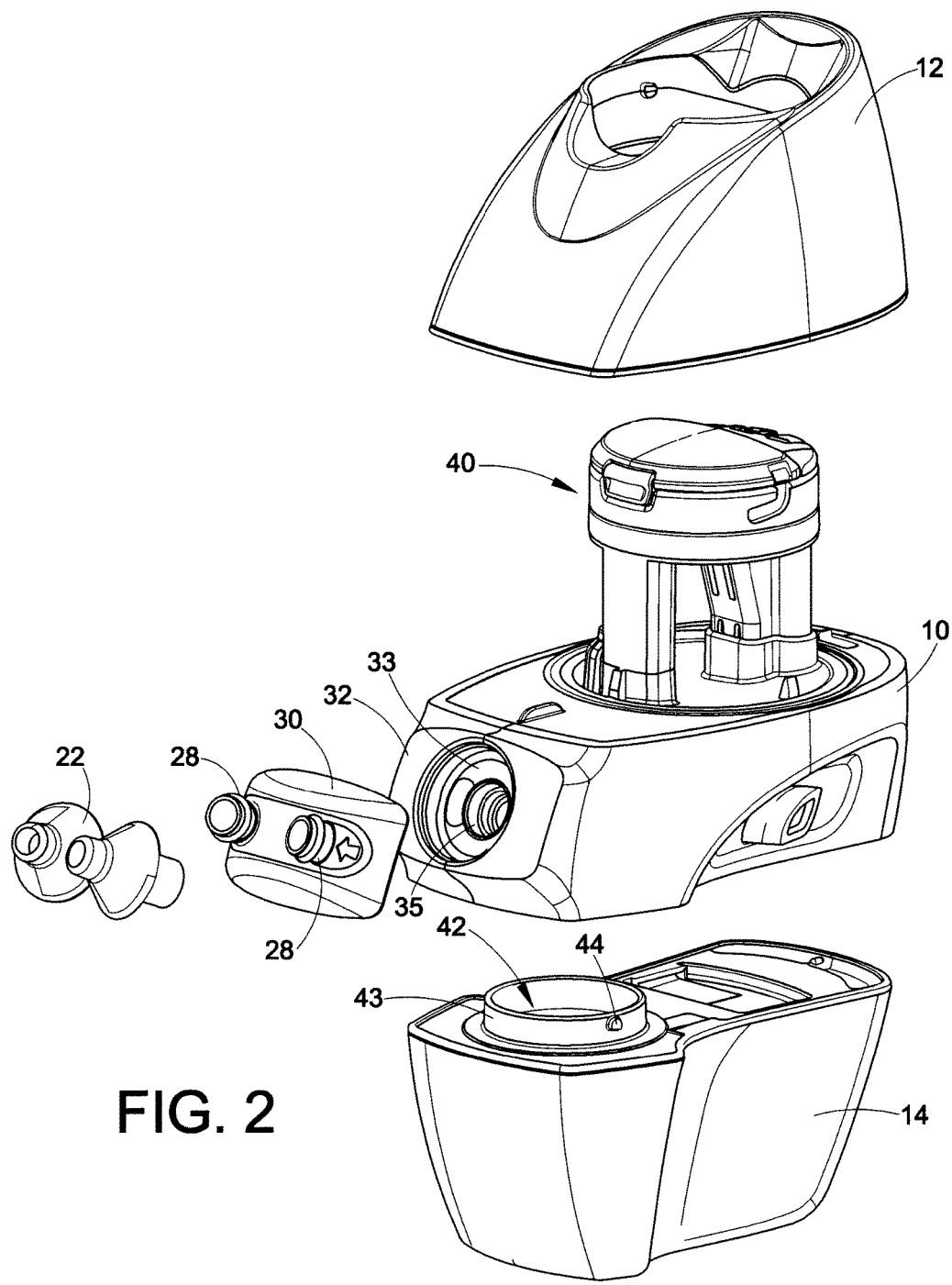
FIG. 2 is an exploded view of the embodiment of FIG. 1.

FIG. 2 shows an exploded version of the assembly as the user might disassemble it for cleaning purposes. One can see therein that the nozzles 22 are intended to be received upon nozzle posts 28 depending from a coaxial turntable mount 30 mounted for fluid sealing engagement on a coaxial turntable receiver 32 in a manner so that the irrigant can be communicated first to one of the nostrils from a first one of the nozzles 22 and received from the nostril through a second nozzle 22. The coaxial turntable mount 30 is readily rotatable so that the direction of flow through the nasal cavity can be selectively reversed upon a desire of the user. One of the nozzles will always communicate fluid out of it regardless of turntable position, while the other nozzle will always receive fluid into it. Thus, a first nozzle is always in communication with the irrigant supply channel 33 in the interface, and the other nozzle is always in communication with the irrigant effluent channel 35.

Figure 3:
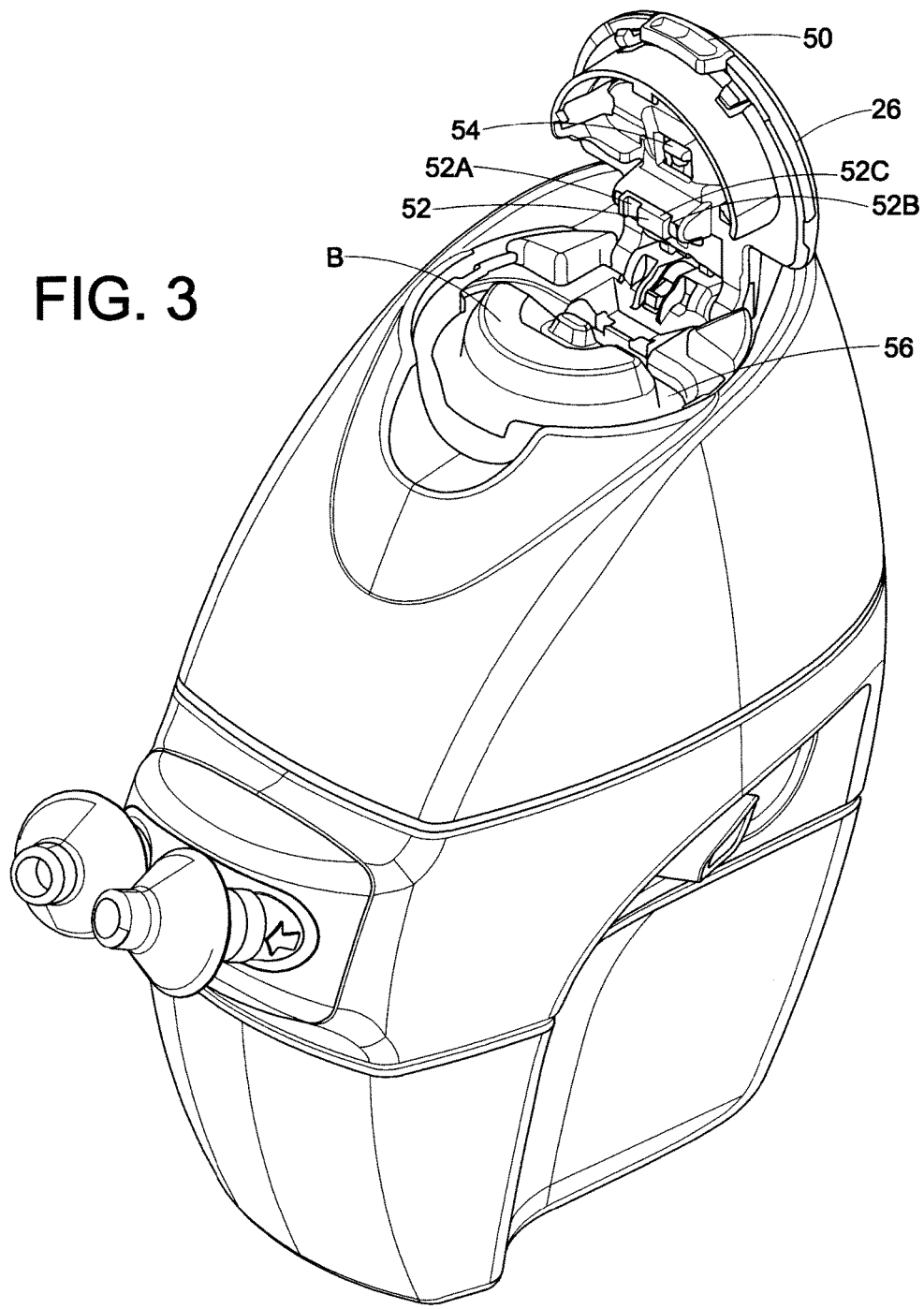
FIG. 3 is a perspective view showing the embodiment of FIG. 1 with an open lid and a saline concentrate capsule received in the device.
Figure 5:
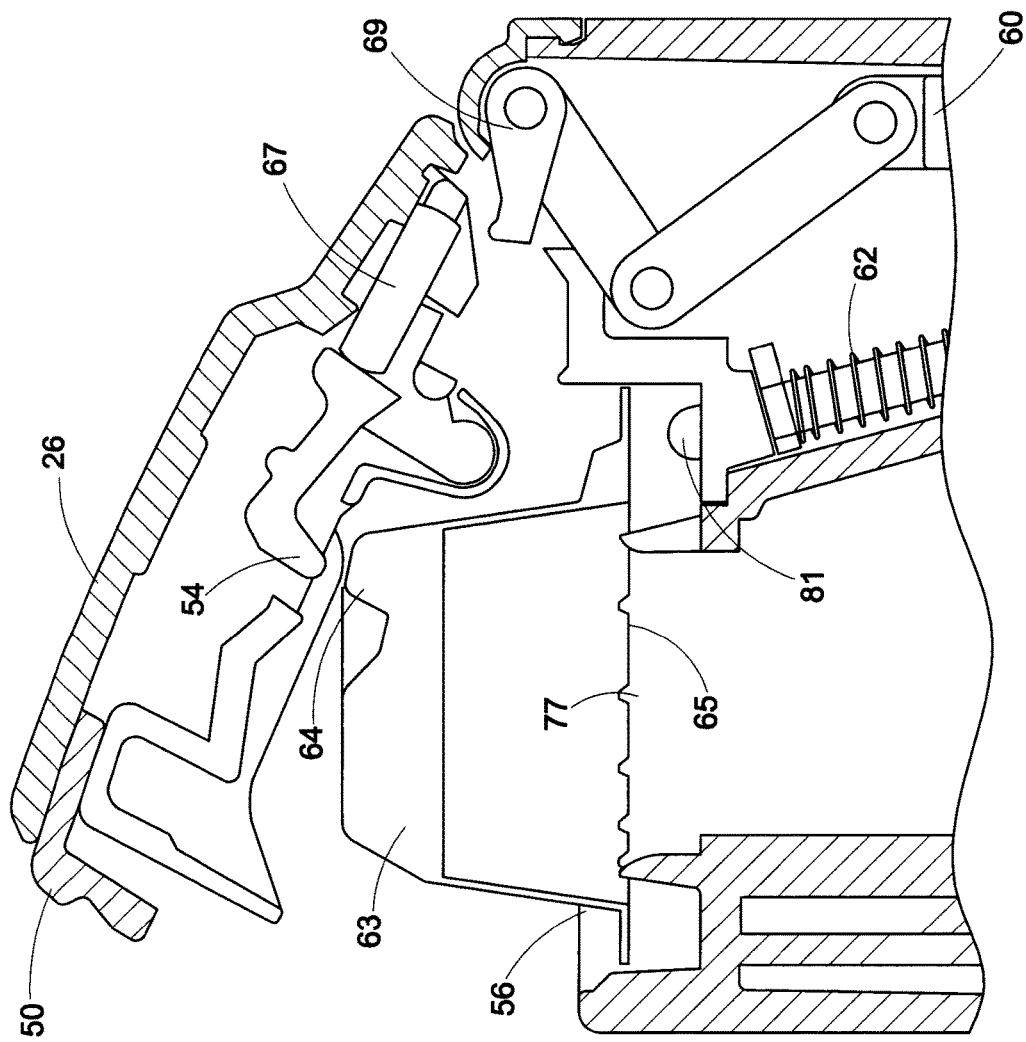
FIG. 5 is a partial sectional view showing lid closing operations.

The mechanics module assembly 10 is seen to include a cartridge or capsule tower assembly 40 having the openable and closeable lid 26 to permit a disposable cartridge B, see FIG. 5, to be received within the tower. FIG. 3 shows the lid 26 open and the capsule B being received therein prior to lid closing and capsule piercing. An authentic capsule B is one that is new and unused.

Figure 6:
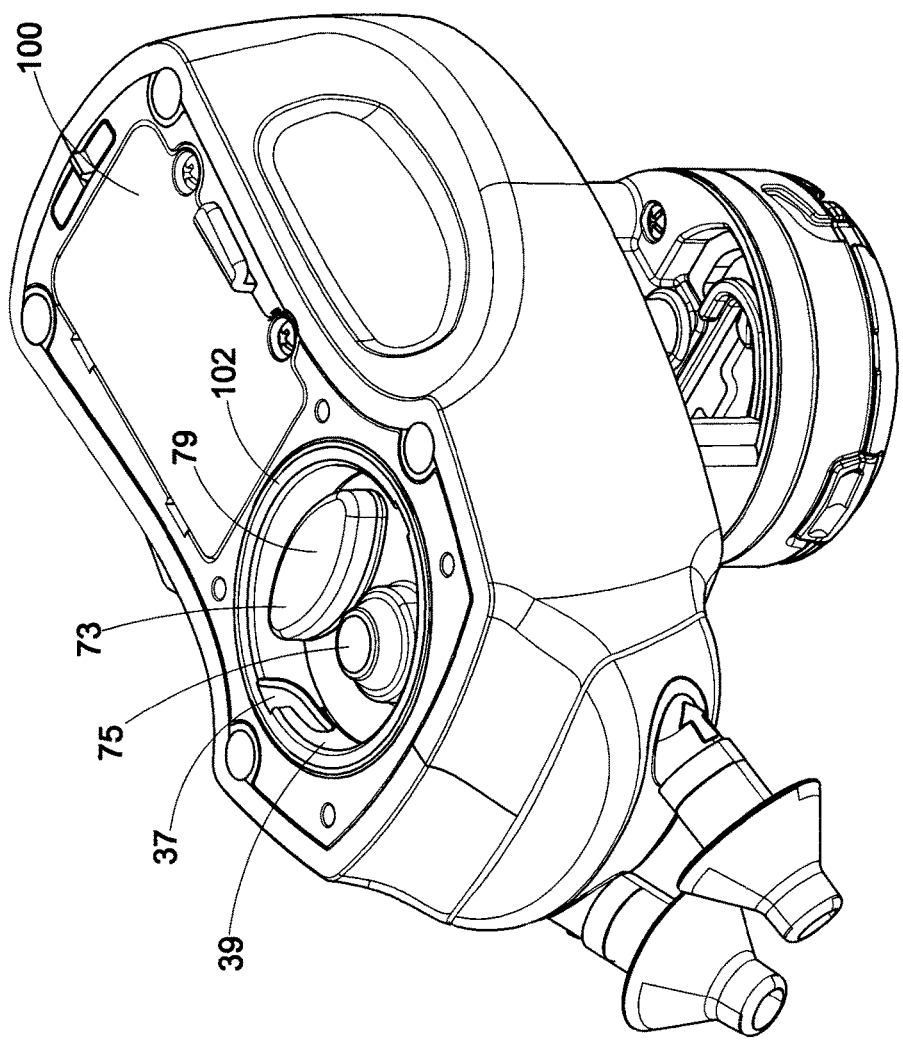
FIG. 6 is a perspective view of the mechanical module, particularly showing the bottom wall thereof.

With continued reference to FIG. 2, when assembled and loaded with irrigant, the system is intended to provide a closed system relative to fluid pressure when sealed against the nasal cavity of a user so that a differential negative pressure resulting in a slight vacuum is applied at the lower reservoir 14 to allow the fluid to fall from the upper reservoir 12 through the mechanical module 10, the nasal interface 30, and the nasal cavity of a user into the lower reservoir 14. The amount of differential pressure is relatively slight, just enough to overcome the combination of human nasal cavity resistance and a declining head pressure due to the evacuating irrigant in the upper reservoir 12. A negative pressure of something between 6 and 24 inches of water should be adequate. It is important that the lower reservoir 14 be air-tight against the mechanics module 10. A bayonet twist mount is effective for this objective including an elastomeric engagement seal 102 on the lower wall of the module 10 contacting the upper outer rim of lower reservoir opening 42. Bayonets 44 can be seen to be disposed on the inlet flange 43 are received in bayonet reception slots 37 in module outlet port 39 (FIG. 6). The lower reservoir 14 also includes a plug 46 (FIG. 4) in its bottom wall for enhanced cleaning access to the interior of the reservoir. In operation, the lower reservoir is first inserted into the mechanics module by alignment between the opening 42 and the module 10 at a slight rotational angle, and then by effecting a slight rotation of the reservoir 14 to the position shown in FIG. 1. A tactile "click" indicates to the user that the reservoir is properly sealed against the module 10. Upper reservoir 12 is similarly applied to the mechanics module 10 by a twisting click indication and similarly must be sealed against the module 10 with an elastomeric seal to preclude the irrigant from leaking out of the reservoir 12 either before or during use. It is not important for the upper reservoir to be air-tight as air is intended to be pulled into the upper reservoir as the fluid is evacuated therefrom to allow the irrigant to properly fall through the system. However, as can be seen with reference to FIGS. 1, 3, and 4, the upper reservoir 12 is closely received about the tower assembly 40.

The lower wall 71 (FIG. 4) of the module 10 includes two fluid openings opposite of opening 42. The first is a pump inlet port 73 for drawing air from the reservoir 12 by the pump 70, and the second is a fluid outlet port 75 for allowing the irrigant effluent, which has cleaned the user's nasal cavity, to fall into the reservoir 14. The air inlet port is protected against drawing irrigant into the module 10 by a float valve and cover 79. The batteries can be replaced through access door 100.

With reference to FIGS. 3 and 5, the lid 26 is opened through a push button 50 typically comprising a latch and catch assembly. The lid 26 includes engaging members 52, 54 specifically intended to engage predetermined areas of the capsule B as an indicator that an authentic capsule B is being used in the system by such members 52, 54 operating in cooperation with the capsule and electrical and mechanical switches to enable fluid flow and pump operation as will be more fully discussed below. The capsule B consists of a crushable plastic housing 63 and a pierceable foil lid 65 that seals to the housing 63. The capsule tower assembly 40 has a recessed seat area 56 that mates with the overall outer configuration of the capsule for a close fitting of the capsule within the tower assembly to facilitate crushing, piercing, and proper camming operation. A plurality of teeth or blades 77 are included in the seat 56 to pierce the foil 65 upon the capsule compression and crushing that results from the lid closing movement, thereby enabling the flow of concentrate therefrom. The capsule compression causes the sealing concentrate to explode out of the capsule upon piercing, thereby facilitating even irrigant mixing throughout.

Figure 4:
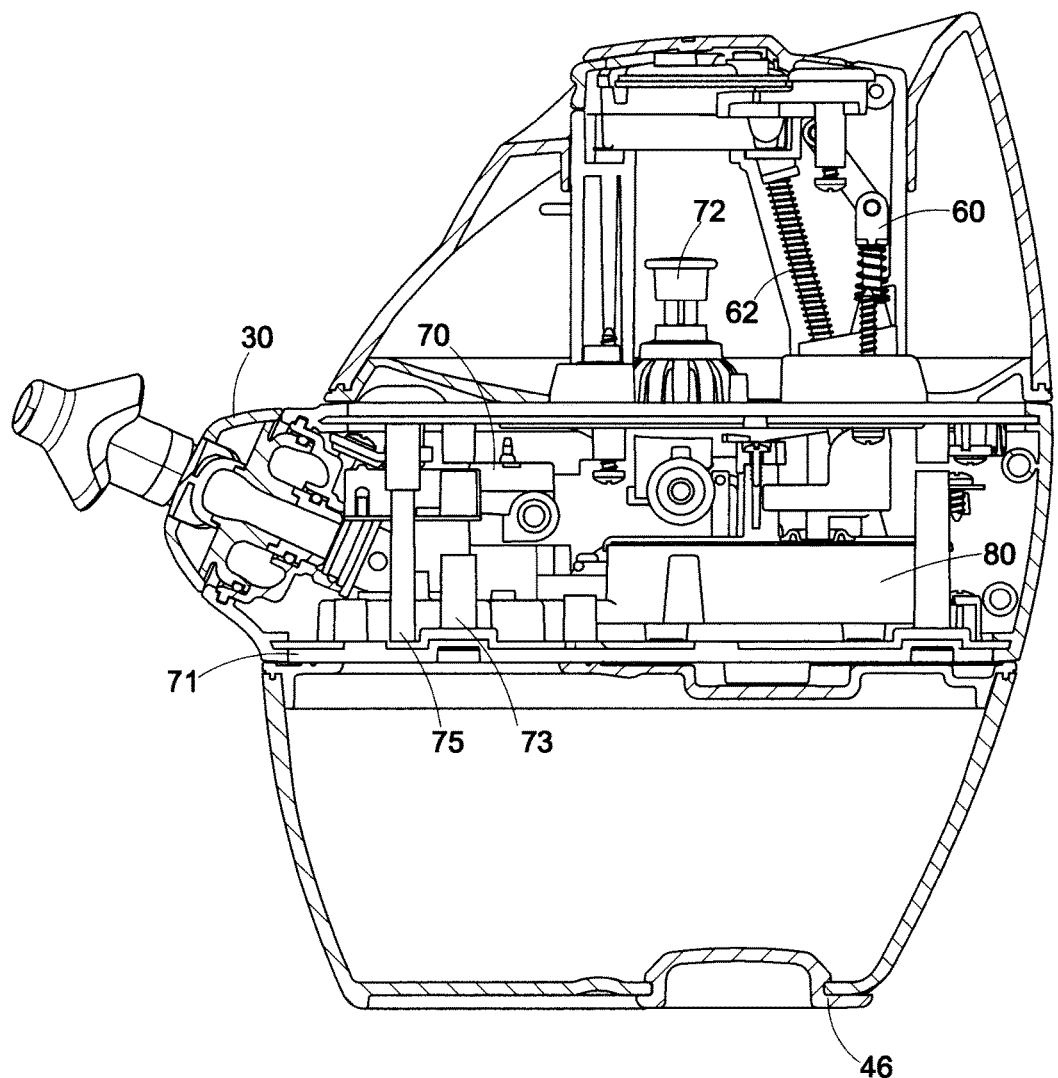
FIG. 4 is a cross sectional view of the embodiment of FIG. 1.

With particular reference to FIGS. 4 and 5 the lock-out systems against a non-authentic capsule are explained. Four different independent lockout actuators are involved in the subject embodiment, and it is within the scope of the intended embodiments to include any one, two, three, or four individually or in any combination to assure a user that only an authentic capsule is being used in the system.

Figure 7:
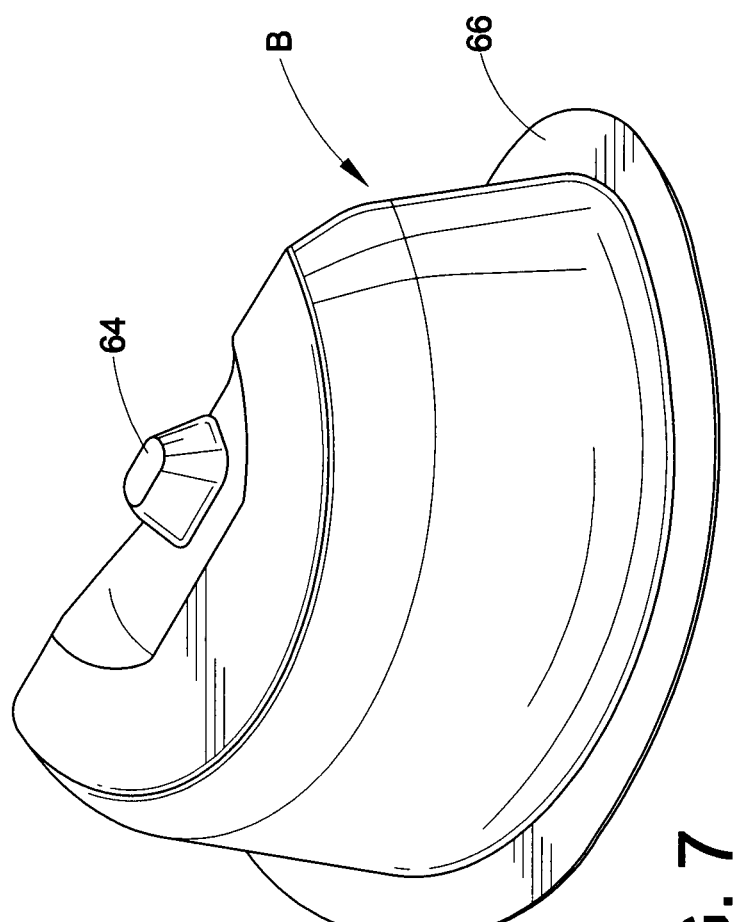
FIG. 7 is a perspective view of a saline concentrate capsule as may be used in the embodiment of FIG. 1.

The capsule B (FIGS. 6 and 7) includes a primary actuation button shown as triggering protrusion or button 64 and a secondary actuation flange shown as a lower wall flange 66. Button 64 is intended to trigger switch actuator 60, and flange 66 is intended to actuate switch rod 62. As lid 26 is closed, lid engaging member or trigger 54 will engage button 64 causing trigger 54 to slide slightly backwards away from the capsule B causing slide 67 to also move over lever 69. As the lid 26 further closes, slide 67 will push down on linkage 60 for two independent results. The end portion of the linkage 60 is disposed to move into engagement and push away a physical lockout member (not shown) that precludes a user from pushing in the on/off switch 24. The failure to operate the device A by successful movement of the on/off switch is the first protective independent actuator. The terminal end of the linkage is also disposed to engage a bellows cover of an electrical circuit interrupt, normally open (not shown), upon lid closing. Failure of the interrupt to be closed by the linkage 60 will preclude electrical power to the system pump. Without evacuating air from the lower reservoir and the fluid passageways, the irrigant cannot pass therethrough. The linkage circuit interrupt is the second protective independent actuator.

As the lid continues to close, engaging member 52 engages the flange 66 causing flange 66 to press down on actuating rod 62 effecting a movement of the rod to also close a second circuit interrupt (not shown). Engaging member 52 comprises opposed engaging projections or surfaces 52A, 52B spaced by recess 52C. The recess 52C is sized to allow the engaging member to pass over the terminal end 81 of rod 62 without moving it when the lid is fully closed, unless an authentic flange 66 bridges the surfaces 52A, 52B during the closing process. In other words, the engaging surfaces 52A, 52B actually only engage the flange 66, which in turn will engage the terminal end 81, causing the push down of the rod 62 with the lid closing. A used or crushed capsule B will likely have a deformation from the flange 66 original position, that may cause the flange to miss the end 81 during the closing. As noted, the purpose of rod 62 movement is to cause the opposite terminal end (not shown) of rod 62 to engage a billows cover of a second circuit interrupt, normally open (not shown), that will preclude power to the pump 70 unless closed. The successful cooperation between the flange 66, the rod 62 and the second circuit interrupt is the third independent system lockout actuator.

Irrigant cannot flow from the upper reservoir until valve 72 is opened. The on/off switch 24 is sized to engage a linkage (not shown) that will open valve 72 as the switch 24 is pushed by the user to a fully on position. As only an authentic capsule will permit the switch 24 to be actuated, the successful opening of the valve 72 by an authentically enabled on/off switch is the fourth independent lockout actuator.

Such a cooperating structure will ensure that only an authentic and a properly mixed and sanitary concentrate is employed within the system. The operation is such that after an authentic capsule B has been properly inserted within the tower assembly, actuators 60 and 62 can enable both the on/off switch 24 and the pump 70. In operation, the user will push on the on/off switch 24, first initiating the pump to begin evacuating air out of the lower reservoir 14. It can be seen that both actuator assemblies are spring biased against enabling actuation. A slight vacuum should then be felt by the user who has properly sealed the interface at their nostrils. Continued pressing of the switch 24 completes the mechanical linkage (not shown) in the module 10 to completely enable the opening of the valve 72 so the irrigant will then begin to flow through the fluid passageways of the mechanical module, through the nasal cavity of the user, and into the lower reservoir 14. The irrigating process continues until the fluid has been drained from the upper reservoir which is apparent to the user either by viewing the fluid through the transparent side walls of the upper reservoir, or until a sensation is detected that the system is no longer sealed against ambient air pressure by the pulling of ambient air through the valve 72 as the upper reservoir 12 has been emptied. Electrical power to the pump is provided by a battery pack 80 although a cord and plug embodiment with a rechargeable battery is alternatively possible.

It is within the scope of the intended embodiments to alternatively dispose electrical control systems, such as sensor and processor based systems, known to one of ordinary skill in the art, in place of selected portions of the foregoing discreet lockout actuators.

Figure 8:
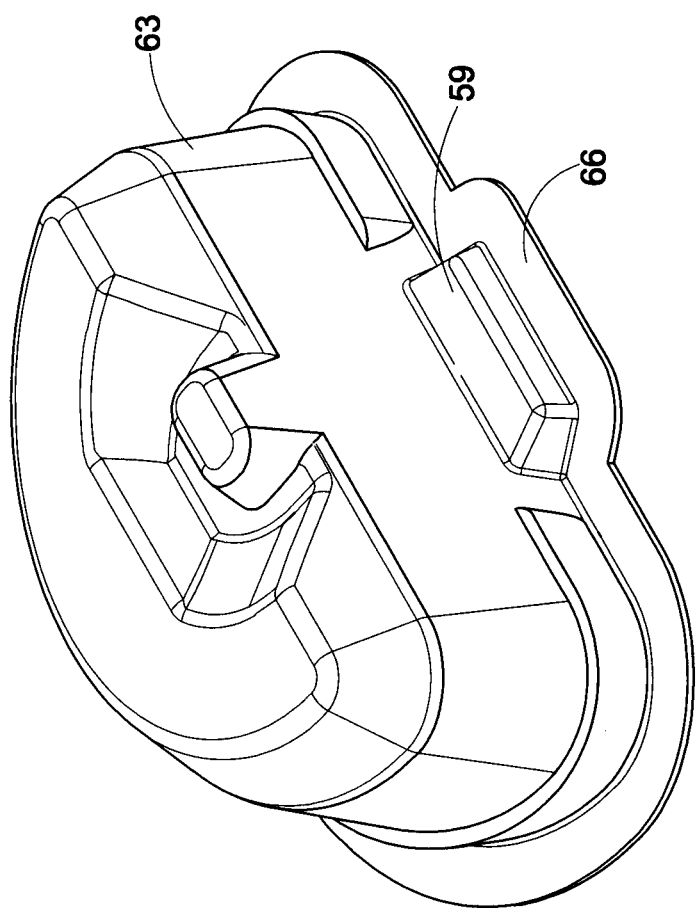
FIG. 8 is an other view of the capsule of FIG. 7.

FIG. 8 shows a better view of the capsule flange portion intended for engagement by engagement surfaces 52A, 52B. It can be seen that the flange is slightly extended over this portion and buttressed by a housing buttress 59, although other buttress configurations could be employed.

Figure 9:
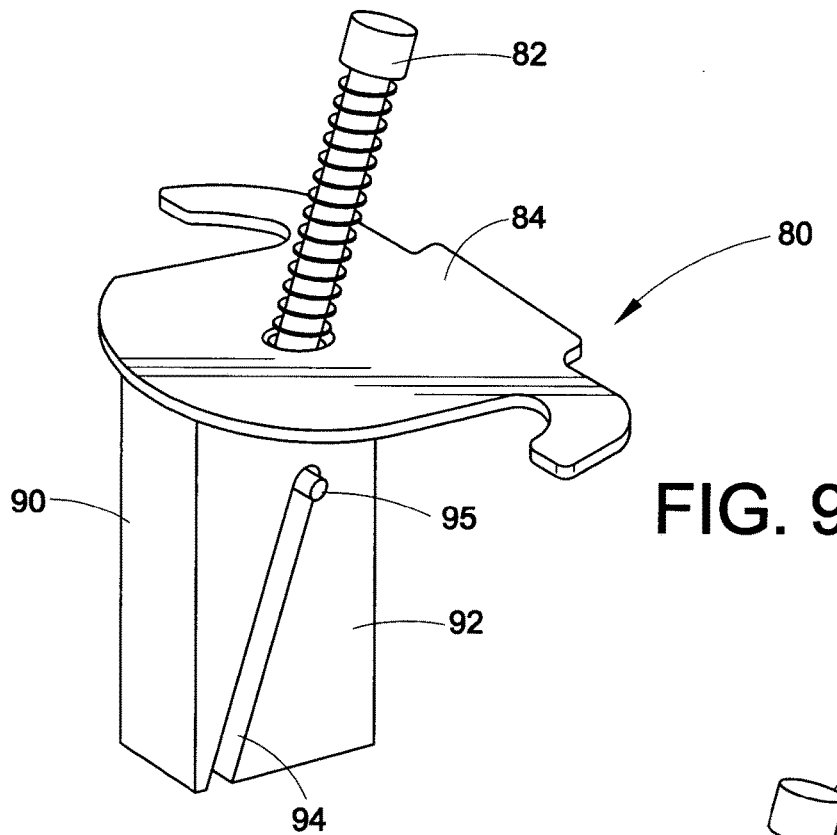
FIG. 9 is an embodiment of faux capsule element.
Figure 10:
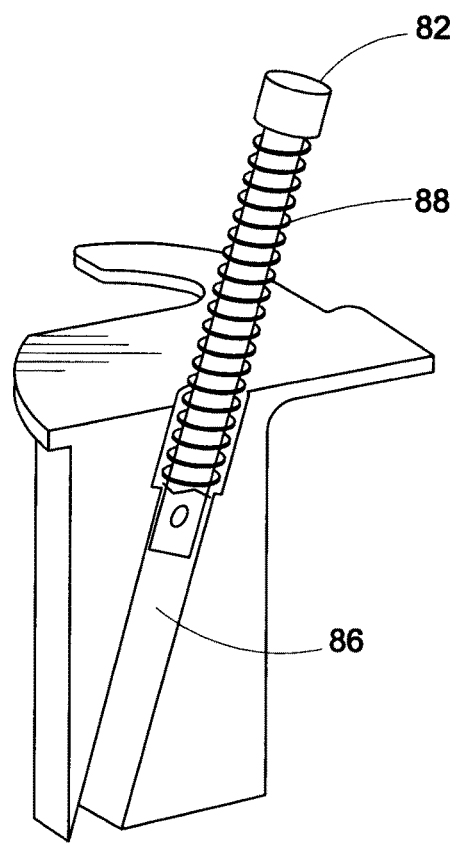
FIG. 10 is a cross sectional view of the embodiment of FIG. 9.

With particular reference to FIGS. 9 and 10, a faux collapsible cartridge embodiment or capsule is shown for testing operation of an embodiment of FIG. 1. The faux cartridge or capsule 80 is comprised of a housing 90 receiving a first spring biased rod 82 to simulate the effect of button 64 of a capsule and a wall 84 to simulate the operation of the capsule flange 66. The faux capsule 80 is received in the tower assembly 40 of the mechanics module 10 so that as the lid 26 is closed, the terminal end of spring biased rod 82 will effectively enable trigger linkage 60 just as button 64 of capsule B would have so triggered it and flange 84, will enable actuating rod 62 just as flange 66 would have. Upon the successful testing of a device A, the faux capsule 80 can be removed from the device, and it can then be used to test a second and additional devices A. Rod 82 is closely received in rod tube or shaft 86 and biased to a fully extended position such as shown in the Figures by spring 88. The rod can be seen to extend from the housing of an angular offset from a centerline of the housing which includes a side wall 92 having a side wall slot 94 wherein a cross pin 96 retains the rod 82 in the shaft 86. The slot 94 is sized to position the terminal end of rod 82 at the proper functional position relative to engaging member 52.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. A capsule comprising a single chamber for holding a single dosage saline solution, the capsule including:
    a crushable housing, the housing comprising:
        a curved sidewall and an opposing flat sidewall,
        a curved top wall, and
        a flange extending from the perimeter of the sidewalls; and
    a pierceable wall, wherein the pierceable wall is sealed to the flange of the housing,
    the crushable housing further comprises:
        a portion of the flat sidewall forming a portion of a button, the button extending upwardly away from the piercable wall, and where the button is partially surrounded by the curved top wall.

2. The capsule of claim 1 wherein the button is formed of the crushable material.

3. The capsule of claim 1 wherein the housing is substantially D-shaped in a cross-section taken in a plane substantially parallel to the actuating flange.

4. The capsule of claim 1 wherein the housing is substantially D-shaped in a cross-section taken in a plane substantially parallel to the pierceable wall.

5. The capsule of claim 1 wherein the housing crushable material is a plastic.

6. The capsule of claim 1 wherein the pierceable wall material is a foil.

* * * * *